(12) United States Patent  (10) Patent No.: US 8,744,192 B2
Ortins et al.  (45) Date of Patent: Jun. 3, 2014

(54) PERSONAL HYGIENE DEVICE USING REAL-TIME OBJECT RECOGNITION AND END-USER FEEDBACK

(75) Inventors: Marc Philip Ortins, Reading, MA (US); George Henry Leal, Hamilton, OH (US); Thomas Aurele Christman, Greenwood, VA (US)

(73) Assignee: The Gillette Company, Boston, MA (US)

( * ) Notice: Subject to any disclaimer, the term of this patent is extended or adjusted under 35 U.S.C. 154(b) by 725 days.

(21) Appl. No.: 12/622,876

(22) Filed: Nov. 20, 2009

(65) Prior Publication Data

US 2010/0170052 A1 Jul. 8, 2010

Related U.S. Application Data

(60) Provisional application No. 61/116,327, filed on Nov. 20, 2008.

(51) Int. Cl.
*G06K 9/46* (2006.01)
(52) U.S. Cl.
USPC .............................. 382/195; 15/106
(58) Field of Classification Search
None
See application file for complete search history.

(56) References Cited

U.S. PATENT DOCUMENTS

| 7,840,042 B2* | 11/2010 | Kriveshko et al. ............ 382/128 |
| 2002/0015934 A1* | 2/2002 | Rubbert et al. .................. 433/29 |
| 2006/0192123 A1* | 8/2006 | Hamelin et al. ........... 250/341.1 |
| 2006/0281042 A1 | 12/2006 | Rizoiu et al. |
| 2007/0136964 A1 | 6/2007 | Dawley |
| 2008/0141476 A1* | 6/2008 | Gatzemeyer et al. ........... 15/105 |
| 2008/0141478 A1* | 6/2008 | Gatzemeyer et al. ........ 15/167.1 |
| 2008/0160477 A1 | 7/2008 | Stookey et al. |
| 2009/0184821 A1 | 7/2009 | Kuris et al. |
| 2009/0185712 A1 | 7/2009 | Wong et al. |

FOREIGN PATENT DOCUMENTS

| IE | 20 060 520 A1 | 2/2008 |
| JP | 07 204370 | 8/1995 |
| WO | WO 2007/112112 | * 10/2007 |

OTHER PUBLICATIONS

Chang et al., "Playful toothbrush: ubicomp technology for teaching tooth brushing to kindergarten children", Proceeding CHI '08 Proceedings of the twenty-sixth annual SIGCHI conference on Human factors in computing systems, pp. 363-372, Published Apr. 2008. ISBN: 978-1-60558-011-1 doi>10.1145/1357054.1357115.*
PCT International Search Report dated Mar. 18, 2010.

* cited by examiner

*Primary Examiner* — Tahmina Ansari
(74) *Attorney, Agent, or Firm* — John P. Colbert; George H. Leal

(57) ABSTRACT

A personal hygiene device includes a personal hygiene implement and a first position member. The personal hygiene device is capable of providing the user with feedback which can assist the user in his/her personal hygiene routines.

15 Claims, 9 Drawing Sheets

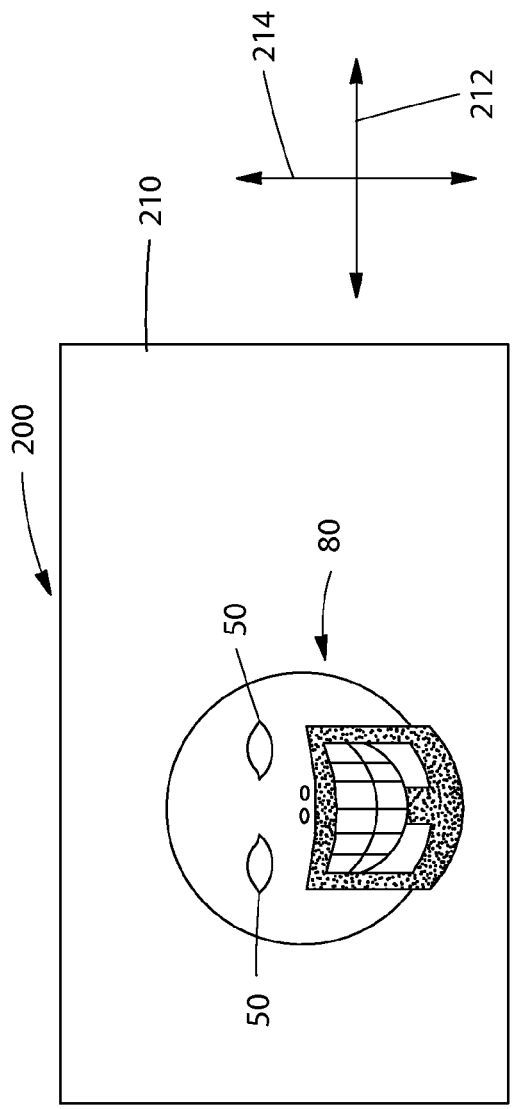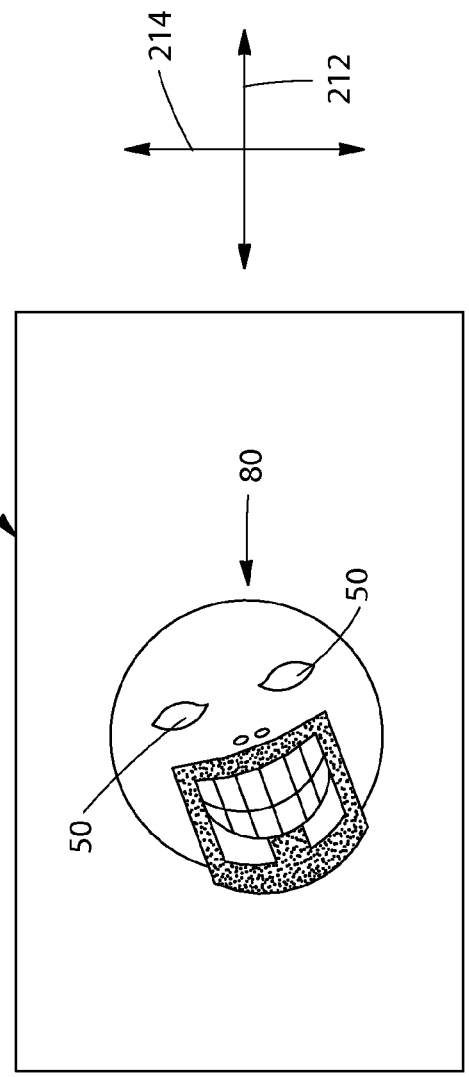
Fig. 2A
Fig. 2B

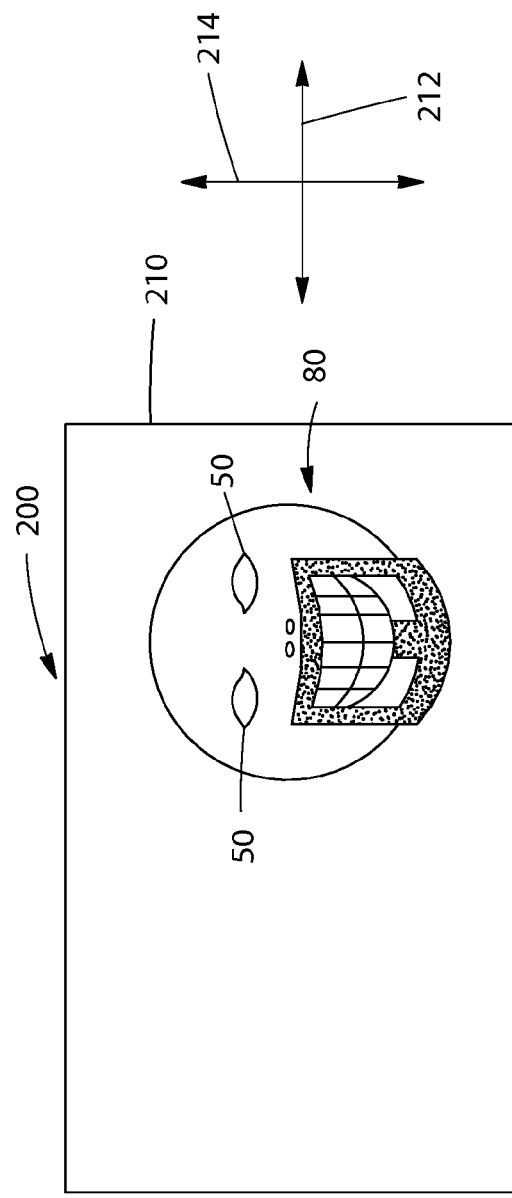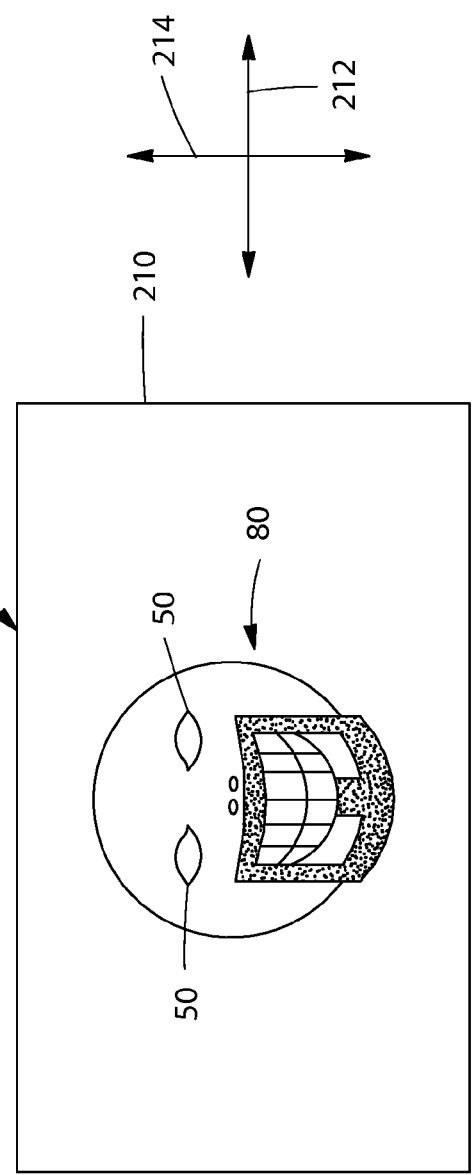

PERSONAL HYGIENE DEVICE USING REAL-TIME OBJECT RECOGNITION AND END-USER FEEDBACK

CROSS REFERENCE TO RELATED APPLICATIONS

This application claims the benefit of U.S. Provisional Application No. 61/116,327, filed Nov. 20, 2008.

FIELD OF THE INVENTION

The present invention pertains to personal hygiene devices, systems and methods, and more particularly, the present invention pertains to personal hygiene devices, systems and methods that include position tracking systems.

BACKGROUND OF THE INVENTION

The effectiveness of brushing teeth in removing plaque from tooth surfaces may be affected by a user's brushing motion, duration and application of force during the brushing process. Accordingly, dental professionals have formed "recommended brushing techniques" which identify and specify such parameters. Those recommended brushing techniques are taught to patients during visits to the dentist. However, once outside the dentist's office, patients often forget and/or abandon the recommended brushing techniques.

Moreover, when a dentist requests a patient to demonstrate their typical brushing technique, such a demonstration is often not accurate or representative of their normal routine. Instead, the patient will generally exaggerate their regular brushing technique due to the dentist's observation. Unfortunately, incorrect brushing habits can negatively impact a person's overall oral health, even if that person utilizes a toothbrush several times a day. For example, incorrect brushing habits may cause a person to consistently neglect cleaning several teeth, or portions of teeth, in an effective manner.

In general, other various personal hygiene routines may also be rendered less effective or ineffective due to a user's improper technique. For example, a man utilizing a manual razor or electric shaver may accidentally miss shaving portions of his face and/or neck making for a slack appearance. As another example, a woman utilizing a manual razor or electric shaver may unintentionally miss shaving portions of her legs. Accordingly, there is a need for personal hygiene devices, systems and methods which aid in the effectiveness of a variety of personal hygiene routines.

SUMMARY OF THE INVENTION

One embodiment of a personal hygiene device includes at least one personal hygiene implement and at least one position member that utilizes object recognition to identify one or more designated features on at least one of a user and the personal hygiene implement.

Another embodiment of a personal hygiene device includes a toothbrush and at least one position member that utilizes object recognition to identify one or more designated features on at least one of a user and the toothbrush.

Another embodiment of a personal hygiene device includes at least one of a razor, shaver and trimmer and at least one position member that utilizes object recognition to identify one or more designated features on at least one of a user, the razor, the shaver and the trimmer.

Another embodiment of a personal hygiene device includes a wash implement and at least one position member that utilizes object recognition to identify one or more designated features on at least one of a user, the washcloth and the sponge.

Another embodiment of a personal hygiene device includes a cosmetics applicator and at least one position member that utilizes object recognition to identify one or more designated features on at least one of a user and the cosmetics applicator.

BRIEF DESCRIPTION OF THE DRAWINGS

FIGS. 2A, 2B, 2C and 2D are depictions of a viewing area of a camera that is part of a personal hygiene device according to one embodiment of the present invention;

DETAILED DESCRIPTION OF THE INVENTION

Definitions

Figure 1:
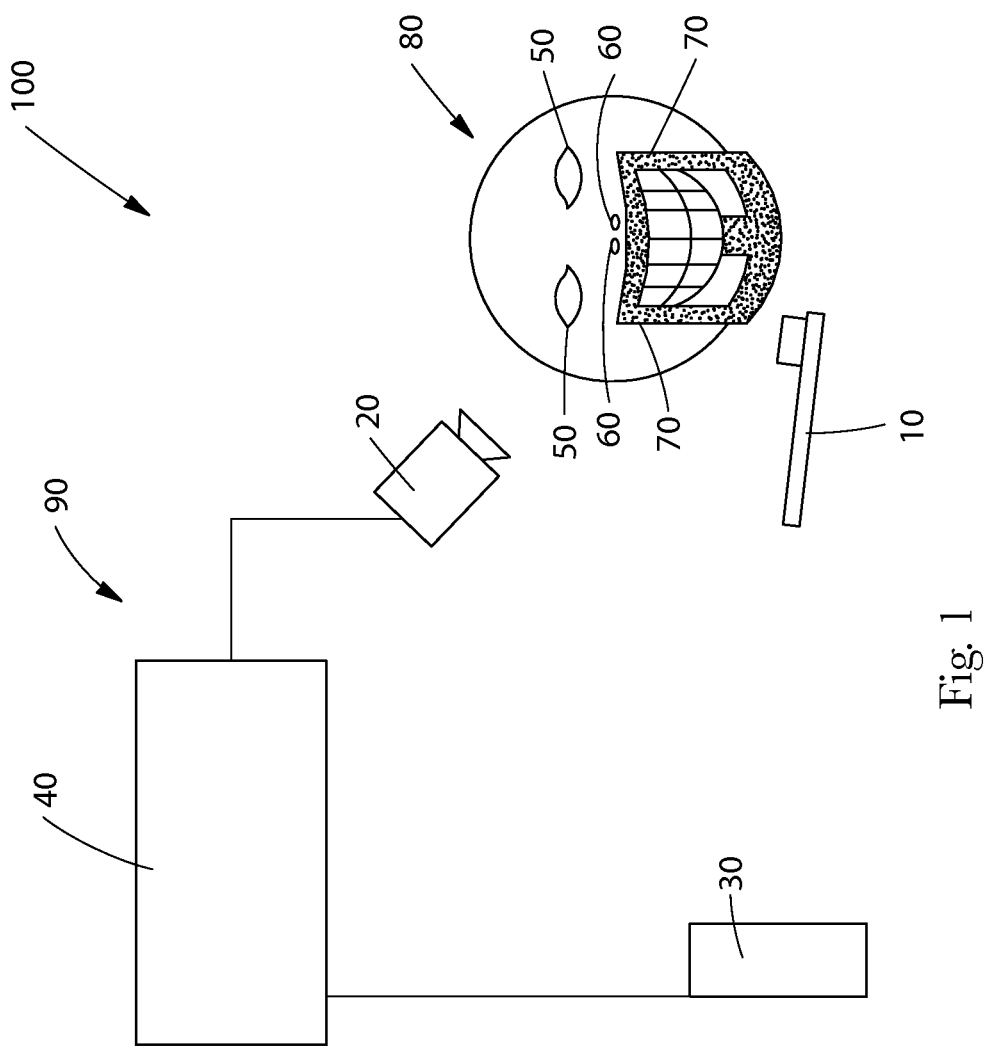
FIG. 1 is a view of a personal hygiene device according to one embodiment of the present invention.

As used herein, the term "personal hygiene" refers to personal cleanliness, as well as personal appearance. Thus it will be understood that improving a user's "personal hygiene" can refer to tooth brushing and face and body washing, as well as body and facial hair shaving and trimming and cosmetics application and removal.

As used herein, the term "personal hygiene implement" refers to any implement which can be utilized for improving personal hygiene or altering personal appearance. Non-limiting suitable examples include manual toothbrushes, powered toothbrushes, men's razors, women's razors, men's shavers, women's shavers, trimmers, luffas, sponges, washcloths, astringent pads, self-tanning applicators and cosmetics brushes and applicators.

As used herein, the term "biological deposits" refers generally to dental plaque, bacteria, tartar, calculus, etc., which are typically regarded as undesirable for good oral hygiene.

As used herein, the term "cosmetic" refers generally to any color cosmetic, hair, nail, or skin care product. Some suitable examples of "cosmetics" include nail varnish, nail polish, eyeliner, mascara, hair colorants, shampoos, conditioners, gels, deodorants, bath oils, bath salts, lipstick, lip gloss, lip liner, lip plumper, lip balm, lip conditioner, lip boosters, foundation, powder, rouge, blush, eye liner, eye shadow, concealer, sunscreens, and the like.

As used herein, the term "markerless" refers to a lack of externally supplied index locators, i.e., markers. Non-limiting examples of such markers include lights, reflectors, textures, colors, sound emitters and/or materials typically foreign to an object with which the markers are associated.

As used herein, the term "image" generally refers to a two-dimensional set of pixels forming a two-dimensional view of a subject within an image plane.

As used herein, the term "image set" generally refers to a set of related two-dimensional images that might be resolved into three-dimensional data.

As used herein, the term "point cloud" generally refers to a three-dimensional set of points forming a three-dimensional view of a subject reconstructed from a number of two-dimensional views. In a three-dimensional image capture system, a number of such point clouds may also be registered and combined into an aggregate point cloud constructed from images captured by a moving camera. Thus it will be understood that the terms "image" and "pixels" generally refer to two-dimensional data and the terms "point cloud" and "points" generally refer to three-dimensional data, unless another meaning is specifically indicated or clear from the context.

As used herein, the terms "three-dimensional surface representation," "digital surface representation," "three-dimensional surface map," and the like, as used herein, are intended to refer to any three-dimensional surface map of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context.

As used herein, the terms "three-dimensional representation" may include any of the three-dimensional surface representations described above, as well as volumetric and other representations, unless a different meaning is explicitly provided or otherwise clear from the context.

As used herein, the terms "render" or "rendering", generally refer to a two-dimensional visualization of a three-dimensional object, such as for display on a monitor. However, it will be understood that three-dimensional rendering technologies exist, and may be usefully employed with the systems and methods disclosed herein. As such, rendering should be interpreted broadly unless a narrower meaning is explicitly provided or otherwise clear from the context.

As used herein, the term "torso" generally refers to a trunk of a body. The trunk does not include legs, arms, and/or the head of the body.

General Description:

A personal hygiene device, system and/or method, in accordance with the present invention, can assist a user in improving their personal hygiene routine. For example, a personal hygiene device of the present invention can assist a user in brushing their teeth more effectively and efficiently. As another example, a personal hygiene device of the present invention can assist a user in shaving or trimming facial or body hair more effectively and/or assist a user in more efficiently obtaining a symmetrical look to desired facial or body hair. As another example, a personal hygiene device of the present invention can assist a user in washing their face and/or body more effectively and efficiently. As yet another example, a personal hygiene device of the present invention can assist a user in applying and removing cosmetic products (e.g., make-up and self-tanning products) more effectively and efficiently. The personal hygiene device of the present invention can assist a user as described above, in part, by measuring the position and/or orientation of a personal hygiene implement, and, in some embodiments, by also measuring the position and/or orientation of at least a portion of the user's body.

As shown in FIG. 1, an embodiment of personal hygiene device 100 may comprise position member 90 and personal hygiene implement 10. In some embodiments, position member 90 may comprise camera 20, display device 30, and receiving unit 40. In those embodiments, camera 20 and display device 30 may be in signal communication with receiving unit 40, thus allowing camera 20 to transmit image data to receiving unit 40, which in turn transmits the image data to display device 30. Additionally, in such embodiments, receiving unit 40 and display device 30 may be integrally formed together. Alternatively, receiving unit 40 may be integrally formed with camera 20 or camera 20 may be integrally formed with display device 30. In other embodiments, receiving unit 40, display device 30, and camera 20 may integrally formed. In yet other embodiments, receiving unit 40, display device 30 and camera 20 may each be discrete components.

In some embodiments, position member 90 can measure the position and/or the orientation of at least a portion of a user's body, and/or at least a portion of personal hygiene implement 10. Position member 90 may perform this task by utilizing a number of different technologies. Non-limiting examples include technologies relating to visual markers, non-visual markers (e.g. audio, sonar, radar, Doppler), object recognition, magnetic, laser and/or, machine vision, etc. In one particular embodiment, position member 90 may utilize markerless technology and be capable of object recognition. Regardless of the technology utilized, the position member 90 may utilize designated features on user 80 and/or personal hygiene implement 10 in order to measure the position and/or the orientation of at least a portion of the user's body and/or at least a portion of the personal hygiene implement 10. An embodiment including a laser scanner is discussed hereafter.

The position member 90 can be programmed to recognize a variety of designated features. For example, embodiments are contemplated where the position member 90 is programmed to recognize marker based designated features (described below) and markerless designated features (described below). In some embodiments, the position member 90 may be programmed to distinguish between designated features of two or more objects. For example, the position member 90 may be programmed to distinguish between a personal hygiene implement and a portion of the body of a user. Some suitable examples of object recognition and/or facial recognition are provided in U.S. Pat. Nos. 5,412,738; 6,128,398; 6,301,370; 7,221,809; U.S. Patent Application Nos. 2001/0043717; 2003/0016869; 2004/0062442; 2006/0251292; 2007/0073439; and 2007/0258645.

For markerless technologies, the designated features can include features of the object for which position/orientation is sought. For example, designated features on user 80 may comprise anatomical landmarks on the body of user 80, or the entire body of user 80. Non-limiting examples of anatomical landmarks on the body of user 80 may include facial landmarks, landmarks on the head, torso landmarks, limb landmarks, fingers, toes, and oral cavity landmarks. With regard to FIG. 1, non-limiting examples of facial landmarks include corners of the eyes 50, nostrils 60, mouth corners 70, combinations thereof and the like. Non-limiting examples of oral landmarks include individual teeth, tooth surfaces, previous dental work, gums, cheeks, lips and a tongue.

Similarly, with regard to markerless technologies, designated features on the personal hygiene implement 10 may comprise color contrast of materials of the personal hygiene implement 10. For example, in embodiments of personal hygiene device 100 that incorporate a toothbrush as personal hygiene implement 10, color contrast between bristles on a head of the toothbrush, as well as color contrast between a first material and a second material on a handle of the toothbrush, may be included as designated features. As another example, in embodiments of personal hygiene device 100 that incorporate a razor as personal hygiene implement 10, color contrast on the razor cartridge and/or color contrast between a first material and a second material on a handle of the razor, may be specific designated features. As yet another example, in embodiments of personal hygiene device 100 that incorporate a sponge, washcloth and/or other cosmetic applicator as personal hygiene implement 10, color contrast within a material or between materials may be included as designated features. Additional designated features of personal hygiene implement 10 include, but are not limited to, printed symbols and/or shapes and three-dimensional geometry designed for visually orienting personal hygiene implement 10.

Additionally, some embodiments of personal hygiene implement 10 have designated features that may include a material contrast. For example, by measuring the temperature gradients between materials of various components of personal hygiene device 10, position member 90 may determine the position/orientation of personal hygiene implement 10. In certain embodiments, the temperature gradients between materials can be measured utilizing infrared optical analytical devices.

With regard to marker based technologies, designated features may include LED's, mirrors, sound emitters, and/or combinations thereof. As an example, these marker based designated features may be adorned by the user in a particular orientation for determining the position and/or orientation of a particular part of the user's body. As yet another example, the marker based designated features may be attached to the personal hygiene implement 10. For example, where the personal hygiene implement 10 is a toothbrush, a plurality of LED's may be attached to the toothbrush handle to differentiate between an x-axis, a y-axis, and a z-axis. Any suitable marker may be utilized for either the user and/or the personal hygiene implement 10.

In some embodiments, the designated features described heretofore may be selected such that the position member 90 is capable of distinguishing between two or more users and/or two or more personal hygiene implements. As an example, the position member 90 may utilize markerless designated features to recognize a first personal hygiene implement and marker based designated features to recognize a second personal hygiene implement. As yet another example, the position member 90 may utilize a first set of designated features to recognize a first personal hygiene implement and a second set of designated features to recognize a second personal hygiene implement. As a specific example, a toothbrush may include a blue and white handle and a razor may include a black and red handle. The position member 90 may be configured such that the position member 90 recognizes the toothbrush and the razor as different personal hygiene implements. Therefore, in certain embodiments of personal hygiene device 100, a first personal hygiene implement may be distinguished from a second personal hygiene implement through the position member 90 recognizing the designated features of the two implements. Likewise, a first user face/body may also be distinguished from a second user face/body through position member recognition of specific designated features.

Marker based position and/or orientation determination for a plurality of objects may be performed in a similar fashion. For example, a toothbrush may utilize a first set of markers while a razor utilizes a second set of markers. The first set of markers and the second set of markers may differ in color, size, temperature, pattern, or the like.

Utilizing the designated features described herein can allow position member 90 to measure the orientation and/or location of at least a portion of the face/body of user 80 and/or the location of at least a portion of personal hygiene implement 10. Referring to FIG. 1, as an example, camera 20 may transmit image data regarding the head of user 80 to receiving unit 40. Based upon the image data and designated features selected, receiving unit 40 may determine the location/orientation of the corners of the eyes 50, nostrils 60 and corners of the mouth 70 of user 80. By determining the location/orientation of the corners of the eyes 50, nostrils 60, and corners of the mouth 70, receiving unit 40 can then determine the location and/or orientation of the head of user 80. As another example, camera 20 may transmit image data regarding personal hygiene implement 10 to receiving unit 40. Based upon the image data and designated features selected, receiving unit 40 may determine the location of personal hygiene implement 10. As yet another example, camera 20 may transmit image data with regard to both user 80 and personal hygiene implement 10. As before, based upon the image data and designated features selected, receiving unit 40 may determine the location of user 80 and personal hygiene implement 10. Generally, camera 20 will be chosen such that the camera can transmit image data to receiving unit 40 at a sufficient rate allowing position member 90 to measure the position and/or orientation of user 80 and/or personal hygiene implement 10 as described above.

Referring to FIGS. 2A and 2B, camera 20 (shown in FIG. 1) may transmit to receiving unit 40 image data regarding the head of user 80 within viewing area 200 of camera 20. Viewing area 200 can be defined by a predetermined number of pixels along x-axis 212 and a predetermined number of pixels along y-axis 214. From the image data provided by camera 20, receiving unit 40 may determine that the orientation of the head of user 80 is substantially upright, if, for example, the corners of the eyes 50 are approximately the same distance along y-axis 214 (this upright position is illustrated in FIG. 2A). In contrast, from the image data provided by camera 20, receiving unit 40 may determine that the orientation of the head of the user is tilted, if, for example, the corners of the eyes 50 are offset by a predetermined distance along y-axis 214 (this tilted position is illustrated in FIG. 2B). The location and/or orientation of personal hygiene implement 10 may be similarly determined utilizing designated features of personal hygiene device 10. In addition to the orientation/position along x-axis 212 and y-axis 214, position member 90 may also be configured to determine the orientation/position of at least a portion of user 80 and/or at least a portion of personal hygiene implement 10 along a z-axis, and/or rotations along each of the axes, i.e. roll, pitch, and yaw.

In some embodiments, camera 20 (shown in FIG. 1) may be mounted inside a bathroom, within a shower, inside a bathroom mirror, on top of a bathroom mirror, or the like. Camera 20 (shown in FIG. 1) may be mounted in any suitable location. Camera 20 (shown in FIG. 1) may be automatically adjustable, manually adjustable or may be fixed in position. In embodiments of personal hygiene device 100 where camera 20 is automatically adjustable, receiving unit 40 may manipulate camera 20 such that the camera tracks the location of specific designated features. As a non-limiting example, if the designated features comprise facial landmarks (e.g., corners of the eyes 50), then camera 20 may be adjusted such that the corners of the eyes 50 are in a certain range of pixels of viewing area 200 of camera 20.

As a specific example, as illustrated in FIG. 2C, the head of user 80 is shown near right edge 210 of viewing area 200 of camera 20 (shown in FIG. 1). In some embodiments of personal hygiene device 100, receiving unit 40 may be configured such that when a selected designated feature is within 10% of the total pixels along x-axis 212 of right edge 210 (counting from left to right along the x-axis), the camera is adjusted to the right such that the selected designated feature is now only within 40% of the total number of pixels along x-axis 212 of right edge 210. As shown in FIG. 2D, the image of user's 80 head and therefore the designated features for the above examples (e.g. corners of the eyes 50) have been shifted to a more central portion of viewing area 200. As another example, where the selected designated feature is within 10% of the total number of pixels along y-axis 214 of bottom edge 211 (counting from top to bottom of the y-axis), receiving unit 40 may manipulate the camera downwards in order to shift the selected designated feature to a more centralized portion of viewing area 200. Similar manipulations are also contemplated for movement of the camera in other various directions. Additionally, receiving unit 40 may automatically adjust the focus of camera 20 (shown in FIG. 1) depending on the selected designated features. A non-limiting example of a suitable adjustable camera is sold by Logitech® located in Fremont, Calif., United States, and sold under the trade name Quick Cam® Orbit AF. Other suitable examples are discussed hereafter.

However, camera 20 (shown in FIG. 1) is not required to be automatically adjustable by receiving unit 40. The position and/or orientation of at least a portion of the body of user 80 and/or at least a portion of personal hygiene implement 10 may also be obtained via camera 20 which is fixed in a particular location. Where camera 20 (shown in FIG. 1) is fixed in a particular location, viewing area 200 of camera 20 may or may not be adjustable via a focus feature. Additionally, when camera 20 (shown in FIG. 1) is fixed in a particular location, the position and/or orientation of user 80 and/or personal hygiene implement 10 will not be measurable so long as the designated features are not identifiable within viewing area 200. Thus, position and/or orientation measurements may be lost when user 80 and/or personal hygiene implement 10 leave camera 20's viewing area 200. Position and/or orientation measurements may be regained once the designated features become identifiable within viewing area 200 once again. Any suitable fixed location camera now or hereafter known in the art may be utilized in conjunction with personal hygiene device 100.

Any suitable camera or camera system now or hereafter known in the art may be utilized with personal hygiene device 100. Non-limiting examples of cameras include multi-aperture scanners as disclosed U.S. Patent Application Publication No. 2004/0155975, which is hereby incorporated by reference in its entirety. While this reference discloses one particular type of multi-aperture scanner system, personal hygiene device 100 may utilize any multi-aperture scanner system suitable for reconstructing a three-dimensional point cloud from a number of two-dimensional images. One particular multi-aperture scanner includes a plurality of apertures including a center aperture positioned along a center optical axis of a lens and any associated imaging hardware. The scanner may include a stereoscopic, triscopic or other multi-camera or other configuration in which a number of cameras or optical paths are maintained in fixed relation to one another to obtain two-dimensional images of an object from a number of slightly different perspectives. The scanner may also include suitable processing for deriving a three-dimensional point cloud from an image set or a number of image sets, or each two-dimensional image set may be transmitted to an external processor such as contained in receiving unit 40 as described heretofore. In further embodiments, camera 20 may employ structured light, laser scanning, direct ranging, or any other technology suitable for acquiring three-dimensional data, or two-dimensional data that can be resolved into three-dimensional data. Additional non-limiting suitable scanners are discussed in WIPO publications WO2007/084768, WO2007/084647 and WO2007/084727, which are all hereby incorporated by reference in their entirety.

In some embodiments of personal hygiene device 100, position member 90 may operate as a three-dimensional image capture system. In such embodiments, a scanner may acquire two-dimensional image sets at a video rate while the scanner is passed over a surface of the subject. The two-dimensional image sets may be forwarded to receiving unit 40 for derivation of three-dimensional point clouds. The three-dimensional data for each newly acquired two-dimensional image set may be derived and fitted or "stitched" to existing three-dimensional data using a number of different techniques. Such a system may employ camera motion estimation to avoid the need for independent tracking of the position of the scanner. One example of camera motion estimation is described in U.S. application Ser. No. 11/270,135, filed on Nov. 9, 2005, which is hereby incorporated by reference in its entirety. However, it will be appreciated that this example is not limiting, and that the principles described herein may be applied to a wide range of three-dimensional image capture systems.

Referring back to FIG. 1, as stated previously, camera 20 may be in signal communication with receiving unit 40 and may send image data thereto. The image data provided to the display device 30 may be processed image data and/or actual image data. For example, the receiving unit 40 may process the actual image data from the camera 20 and provide the processed image data to display device 30. In another example, receiving unit 40 may provide the actual image data from camera 20 to display device 30. As yet another example, receiving unit 40 may provide both processed image data and actual image data to display device 30.

Any suitable receiving unit now or hereafter known in the art can be utilized in embodiments of personal hygiene device 100. For example, receiving unit 40 may be a computer, for example, a personal computer or other processing device. In one specific embodiment, the computer may be a personal computer with a dual 2.8 GHz Opteron central processing unit, 2 gigabytes of random access memory, a TYAN Thunder K8WE motherboard, and a 250 gigabyte, 10,000 rpm hard drive. This computer system may be operated to capture approximately 1,500 points per image set in real time using the techniques described herein, and store an aggregated point cloud of over one million points. As used herein, the term "real time" means generally with no observable latency between processing and display. In a video-based scanning system, real time more specifically refers to processing within the time between frames or processing within the time of multiple frames of video data, which may vary according to specific video technologies between about five frames per second and about thirty frames per second. For example, "real time" may be considered to be about a five frame video data lag between the processing and the display. More generally, processing capabilities of the computer may vary according to the size of the subject, the speed of image acquisition, and the desired spatial resolution of three-dimensional points. The computer may also include peripheral devices such as a keyboard, a mouse for user interaction with the computer, and in some embodiments as discussed above, display device 30.

Regardless of the type of image data transferred to display device 30, a visual representation provided on display device 30 may assist the user in their personal hygiene routine. For example, display device 30 may display a visual representation of at least a portion of personal hygiene implement 10 (e.g. head of a toothbrush or cosmetic applicator) during use. As another example, display device 30 may display a visual representation of at least a portion of user 80's body (e.g. oral cavity, face, torso or legs). As yet another example, display device 30 may display a visual representation of both a portion of personal hygiene implement 10 and a portion of user 80's body. Alternately, display device 30 may only display a visual representation of lights provided by a LED display. Alternately still, display device 30 may not even display a visual representation, as display device 30 may emit sounds or vibrations utilized in conjunction or in place of a visual representation.

In one specific embodiment of personal hygiene device 100, a plurality of light emitting diodes may be utilized as display device 30 to signify certain conditions. For example, a light emitting diode or a plurality of light emitting diodes can be energized to signify a particular event in a personal hygiene routine. For example, particular events may include brushing for a sufficient period of time or effectively cleaning a predetermined area.

Figure 3:
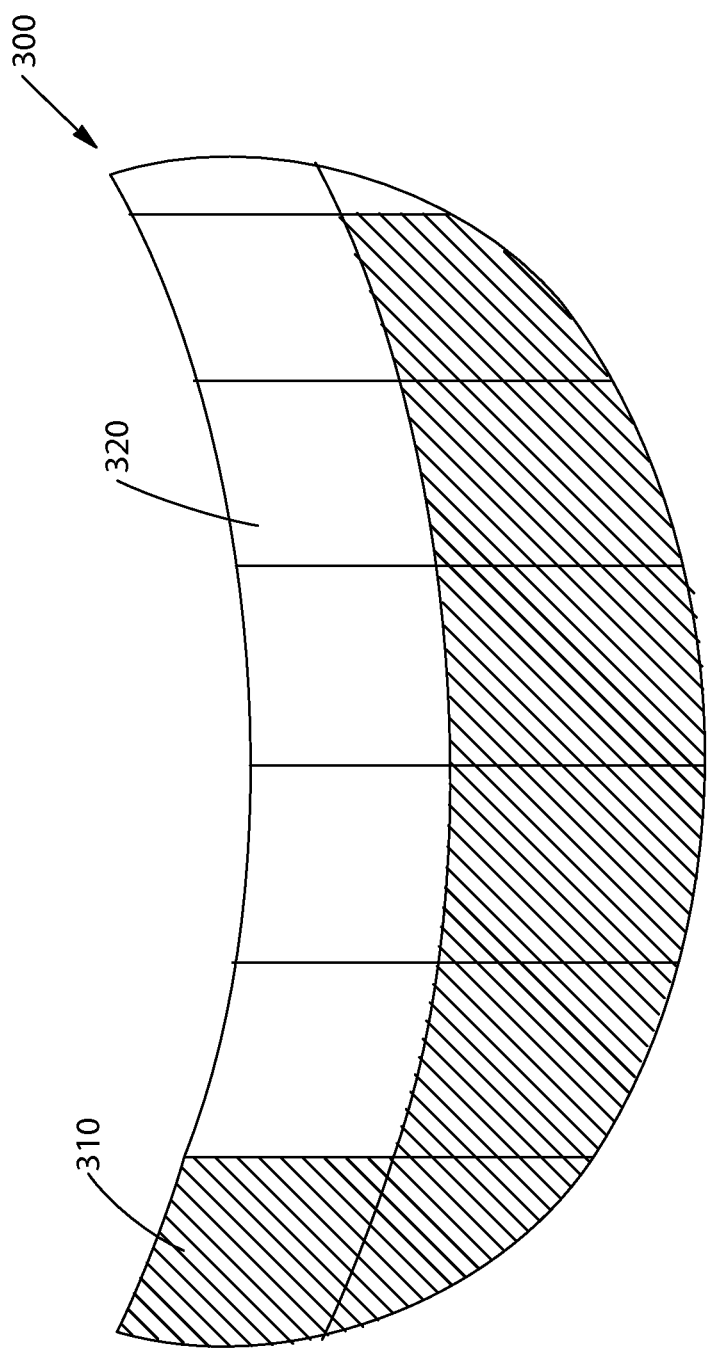
FIG. 3 is an image of a simulated oral cavity that can be shown on a display device that is part of a personal hygiene device according to one embodiment of the present invention.

In particular embodiments, the visual representation can be a previously stored image in receiving unit 40. Alternatively, the visual representation can be provided to receiving unit 40 in real time utilizing camera 20. In other embodiments, display device 30 may provide a generic visual representation (e.g., a visual representation of a generic oral cavity), which only approximates the oral cavity of the user. In other embodiments, display device 30 may display a simulated or cartoon visual representation (e.g., a visual representation of a simulated oral cavity, as illustrated in FIG. 3).

In some embodiments (in particular, those in which a portion of user 80's oral cavity is displayed in real time), a second camera (not shown) may be implemented in personal hygiene implement 10. In other embodiments, camera 20 may be the sole camera in personal hygiene device 100 and may be implemented in personal hygiene implement 10 and provide image data from the oral cavity of user 80 to receiving unit 40. In these embodiments, the designated features utilized may include features of the oral cavity of user 80 such that receiving unit 40 can identify predetermined oral surfaces within the oral cavity and thereby identify the orientation/position of the head of user 80 with respect to personal hygiene implement 10.

Regardless of the existence of a second camera or whether camera 20 is implemented within personal hygiene implement 10, a camera or cameras may be disposed at, on, or in any suitable location of personal hygiene device 100. For example, the camera may be disposed in the head of personal hygiene implement 10, in the handle of personal hygiene implement 10 and/or in the neck of personal hygiene implement 10. Other embodiments include camera 20 and/or a second camera implemented in a separate probe. For example, the separate probe could be detachable from personal hygiene implement 10. As yet another example, the separate probe could be a separate implement which is configured for intra-oral insertion.

Similarly, any suitable display device now or hereafter known in the art can be utilized with embodiments of personal hygiene device 100. Display device 30 may be a touch screen display capable of receiving user input through direct, physical interaction with the display. Display device 30 may include any display suitable for video or other rate rendering at a level of detail corresponding to the acquired data. Suitable displays include cathode ray tube displays, liquid crystal displays, light emitting diode displays, fixed segment displays, plasma displays, dot matrix displays, combinations thereof and the like. In some embodiments, display device 30 may include a touch screen interface using, for example capacitive, resistive, or surface acoustic wave (also referred to as dispersive signal) touch screen technologies, or any other suitable technology for sensing physical interaction with display device 30.

Some embodiments of personal hygiene device 100 are stationed in a bathroom where the majority of personal hygiene routines occur. In such embodiments, it may be desirable for the display device to be relatively small such that the amount of space taken up by the display device is minimal. In contrast, in locations where space is not a concern, a larger display may be desirable.

Communications between receiving unit 40, camera 20, and display device 30, may include any suitable communications link. Some examples of suitable communication links include wired connections, wireless connections, and/or combinations thereof. Non-limiting specific examples of wireless connections include connections based on IEEE 802.11 (also known as wireless Ethernet), BlueTooth, radio frequency, infrared and combinations thereof. Additionally, some embodiments incorporate secured wireless image transmission from camera 20 to receiving unit 40. In such embodiments, receiving unit 40 may generate control signals to camera 20 which, in addition to image acquisition commands, may include conventional camera controls such as focus or zoom.

Oral Hygiene Embodiments

Referring again to FIG. 1, the position and/or orientation data can be utilized in conjunction with the personal hygiene routine of a user in a number of different ways. For example, in embodiments of personal hygiene device 100 where personal hygiene implement 10 is a toothbrush, receiving unit 40 can monitor the teeth which have been effectively brushed and the teeth which have not been effectively brushed based upon the gathered position data for the toothbrush and the head of user 80. Additionally, receiving unit 40 may provide processed image data to display device 30 providing an indication of which teeth have been brushed and teeth which have not been brushed.

As shown in FIG. 3, the display device may provide visual representation 300 of a simulated portion of an oral cavity, such as a plurality of teeth. The image may include teeth of a first color 310 and teeth of a second color 320 to indicate a hygiene status of portions of the user's oral cavity. For example, in certain embodiments, teeth of first color 310 may designate teeth which are yet to be effectively brushed and teeth of second color 320 may designate teeth which have been effectively brushed. Any colors may be utilized for first color 310 and second color 320, and such colors should be distinguishable from one another. In alternate embodiments, any number, varieties and shades of colors may be utilized to indicate any number or variety of hygiene statuses of particular portions of the user's oral cavity.

Additionally, visual representation 300 of a simulated portion of an oral cavity may also further include soft tissues, such as gums and/or a tongue. In these embodiments, one or more of these simulated soft tissues may utilize first color 310 or second color 320 depending on the soft tissue hygiene status (e.g., depending on whether or not user 80 has performed a cleaning operation on them). In one non-illustrated embodiment of personal hygiene device 100, visual representation 300 of a simulated portion of an oral cavity may include a tongue which is shown in first color 310 prior to the tongue being cleaned. When user 80 performs a cleaning operation on the tongue, visual representation 300 may show the tongue in second color 320 to indicate that a cleaning operation has been performed on the tongue.

Moreover, embodiments are contemplated where personal hygiene implement 10 is a toothbrush which includes a tongue cleaner. In these embodiments, position member 90 may determine the orientation of the toothbrush such that if user 80 attempts to utilize the bristles of the toothbrush instead of the tongue cleaner to cleanse their tongue, the image may continue to show the tongue in first color 310 because the proper cleaning operation was not performed on the tongue. Likewise, where user 80 attempts to brush their teeth with a tongue cleaner instead of the bristles of the toothbrush, the visual representation 300 may continue to show the teeth in first color 310 until the user 80 utilizes the bristles of the toothbrush to clean the teeth.

Any suitable tongue cleaner may be utilized on personal hygiene implement 10. Non-limiting examples are disclosed in U.S. Pat. Nos. 5,005,246; 5,735,864; 5,766,193; 5,779,654; 5,792,159; 5,810,856; 6,571,417; 6,792,642; 6,820,299; 6,859,969; 6,944,903; 7,047,589; 7,051,394 and 7,181,799; U.S. Patent Application Publication Nos. 2004/0134007; 2004/0255416; 2005/0000043; 2005/0000049; 2005/0038461; 2005/0166344; 2005/0210612; 2005/0210613; 2006/0010628; 2006/0026784 and 2007/0049956; WO Publication Nos. 2001/045573 and 2007/140959; and German reference nos. DE202005009026U1 and DE 3114507A1, or combinations thereof, which are all hereby incorporated by reference in their entirety.

Figure 4B:
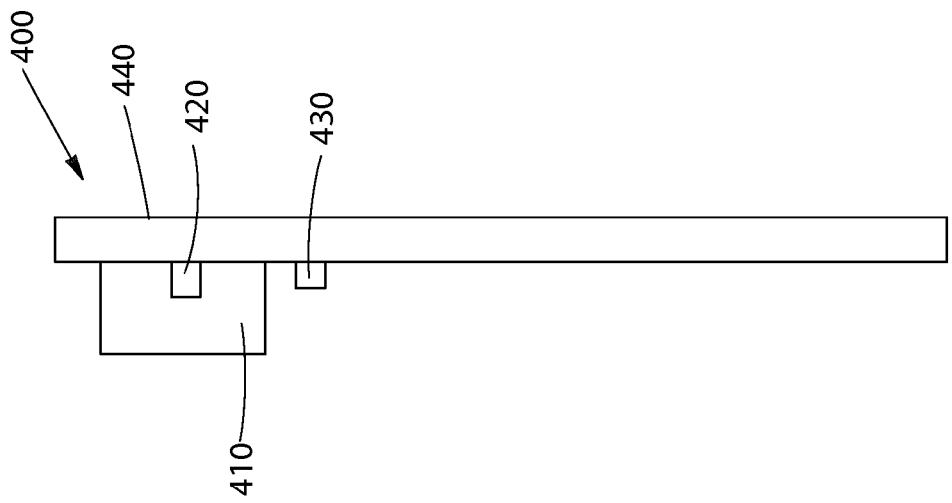
FIG. 4B is a side view of a toothbrush that is part of a personal hygiene device according to one embodiment of the present invention.
Figure 4A:
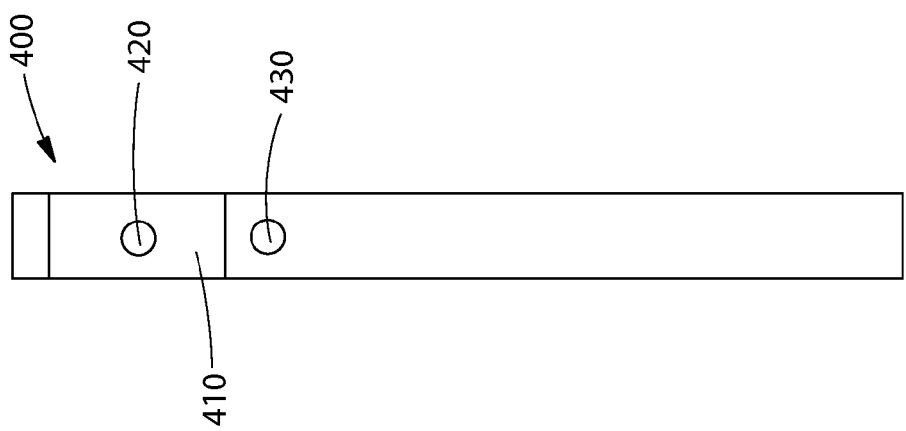
FIG. 4A is a front view of a toothbrush that is part of a personal hygiene device according to one embodiment of the present invention.

In addition to identifying which oral surfaces have been cleaned, embodiments are contemplated where the toothbrush may provide the user 80 with feedback regarding the efficiency of their brushing technique. For example, in some embodiments, a toothbrush, as shown in FIGS. 4A and 4B, may comprise an electromagnetic energy source 420, a cleaning element field 410, and a detection device 430. The electromagnetic energy source 420 may be selected to induce auto-fluorescence and/or secondary fluorescence in dental plaque or other biological deposits within the oral cavity or may be selected to induce secondary fluorescence in a disclosing agent. Regardless of whether auto-fluorescence or secondary fluorescence is utilized, electromagnetic energy source 420 may emit light in having wavelengths of from about 380 nm to about 780 nm, or any individual number within the range. In some embodiments, electromagnetic energy source 420 may emit electromagnetic energy having wavelengths which are greater than about 380 nm, greater than about 390 nm, greater than about 400 nm, greater than about 410 nm, greater than about 420 nm, greater than about 430 nm, greater than about 440 nm, greater than about 450 nm, greater than about 460 nm, greater than about 470 nm, greater than about 480 nm, greater than about 490 nm, greater than about 500 nm, greater than about 510 nm, greater than about 520 nm, greater than about 530 nm, greater than about 540 nm, greater than about 550 nm, greater than about 560 nm, greater than about 570 nm, greater than about 580 nm, greater than about 590 nm, greater than about 600 nm, greater than about 610 nm, greater than about 620 nm, greater than about 630 nm, greater than about 640 nm, greater than about 650 nm, greater than about 660 nm, greater than about 670 nm, greater than about 680 nm, greater than about 690 nm, greater than about 700 nm, greater than about 710 nm, greater than about 720 nm, greater than about 730 nm, greater than about 740 nm, greater than about 750 nm, greater than about 760 nm and/or less than about 780 nm, less than about 770 nm, less than about 760 nm, less than about 750 nm, less than about 740 nm, less than about 730 nm, less than about 720 nm, less than about 710 nm, less than about 700 nm, less than about 690 nm, less than about 680 nm, less than about 670 nm, less than about 660 nm, less than about 650 nm, less than about 640 nm, less than about 630 nm, less than about 620 nm, less than about 610 nm, less than about 600 nm, less than about 590 nm, less than about 580 nm, less than about 570 nm, less than about 560 nm, less than about 550 nm, less than about 540 nm, less than about 530 nm, less than about 520 nm, less than about 510 nm, less than about 500 nm, less than about 490 nm, less than about 480 nm, less than about 470 nm, less than about 460 nm, less than about 450 nm, less than about 440 nm, less than about 430 nm, less than about 420 nm, less than about 410 nm, or less than about 400 nm.

In auto-fluorescence embodiments, a user exposes biological deposits to emitted electromagnetic energy from electromagnetic energy source 420. Without wishing to be bound by theory, it is believed that the biological deposits absorb at least a portion of the electromagnetic energy and reflects a portion of that electromagnetic energy. The biological deposit also emits electromagnetic radiation having a different wavelength or range of wavelengths than that of the electromagnetic energy emitted by electromagnetic energy source 420. The auto-fluorescence may produce a visible color contrast and/or a detectable color contrast between clean tooth surfaces and the biological deposits and/or may produce detectable wavelength contrast between clean tooth surfaces and the biological deposits. Substantial overlap may occur between the reflected wavelength ranges and the fluoresced wavelength ranges.

Figure 5A:
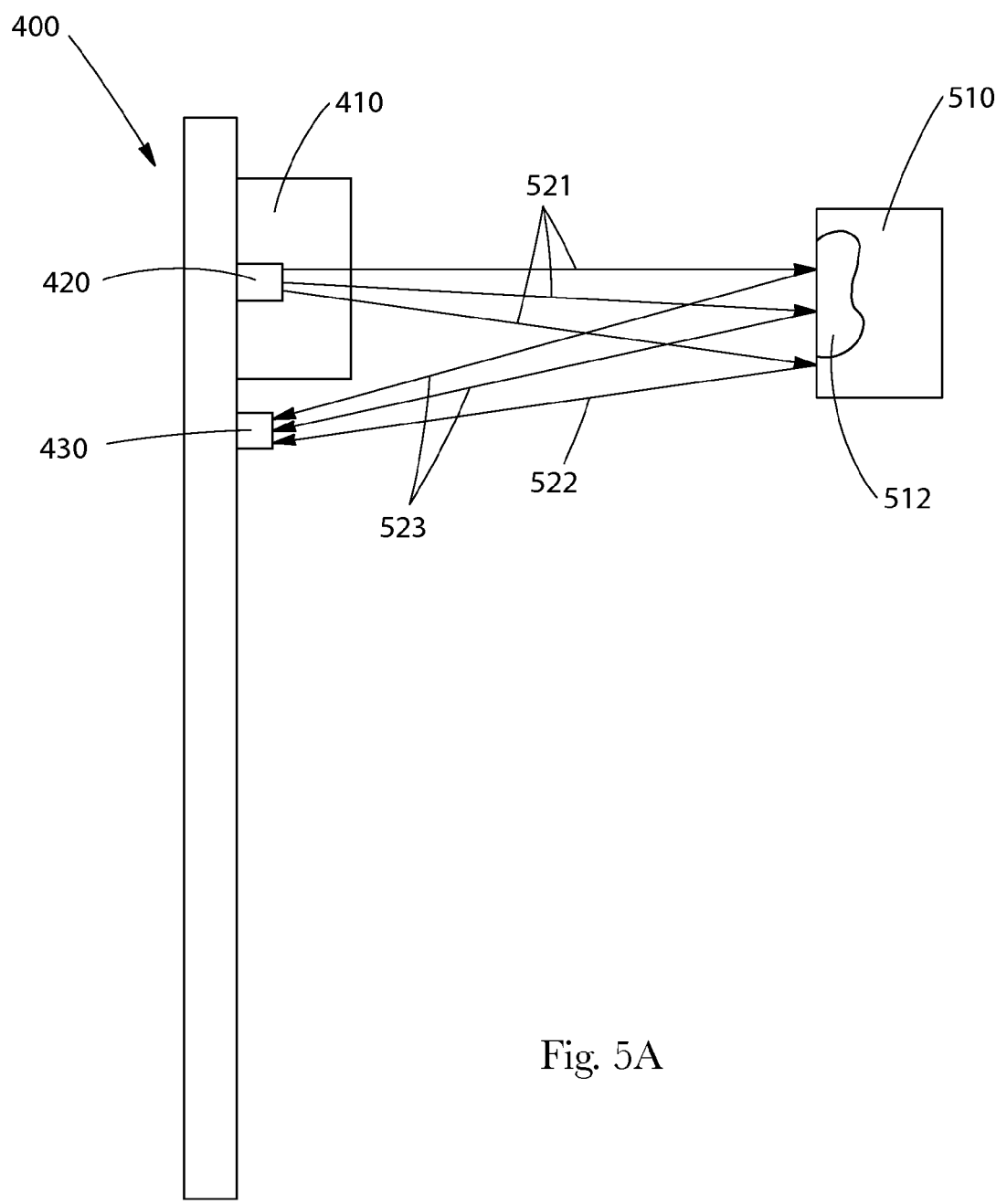
FIG. 5A is a depiction of a toothbrush that is part of a personal hygiene device according to one embodiment of the present invention and a tooth.

Referring to FIG. 5A, as energy source 420 emits electromagnetic energy 521 toward and/or into the oral cavity, a portion of that energy may reflect (reflected energy 522) from oral cavity surfaces such as teeth 510, gums and a tongue. In addition, as set forth above, a portion of the energy transmitted from energy source 420 may be absorbed by biological deposit 512 within the oral cavity at a location having a particular condition (e.g., at a plaque location). At least a portion of the absorbed energy may be emitted by the biological deposit 512 as fluorescent energy, thereby highlighting a condition within the oral cavity (e.g., plaque buildup).

In certain situations, reflected energy 522 from the oral cavity surfaces can have an intensity which can overpower the fluorescent energy emitted from the biological deposit 512. Accordingly, this overpowering by reflected energy 522 (e.g., light less than about 500 nm) may make it difficult for a user to observe and/or distinguish the fluorescent energy from reflected energy 522. Additionally, this overpowering by reflected energy 522 may compromise the accuracy of energy measurement by detection device 430, potentially leading to erroneous results. Additionally, in some cases, ambient light may also interfere with the detection/observation of the fluorescent energy as distinguished from the electromagnetic energy of ambient light.

Figure 5B:
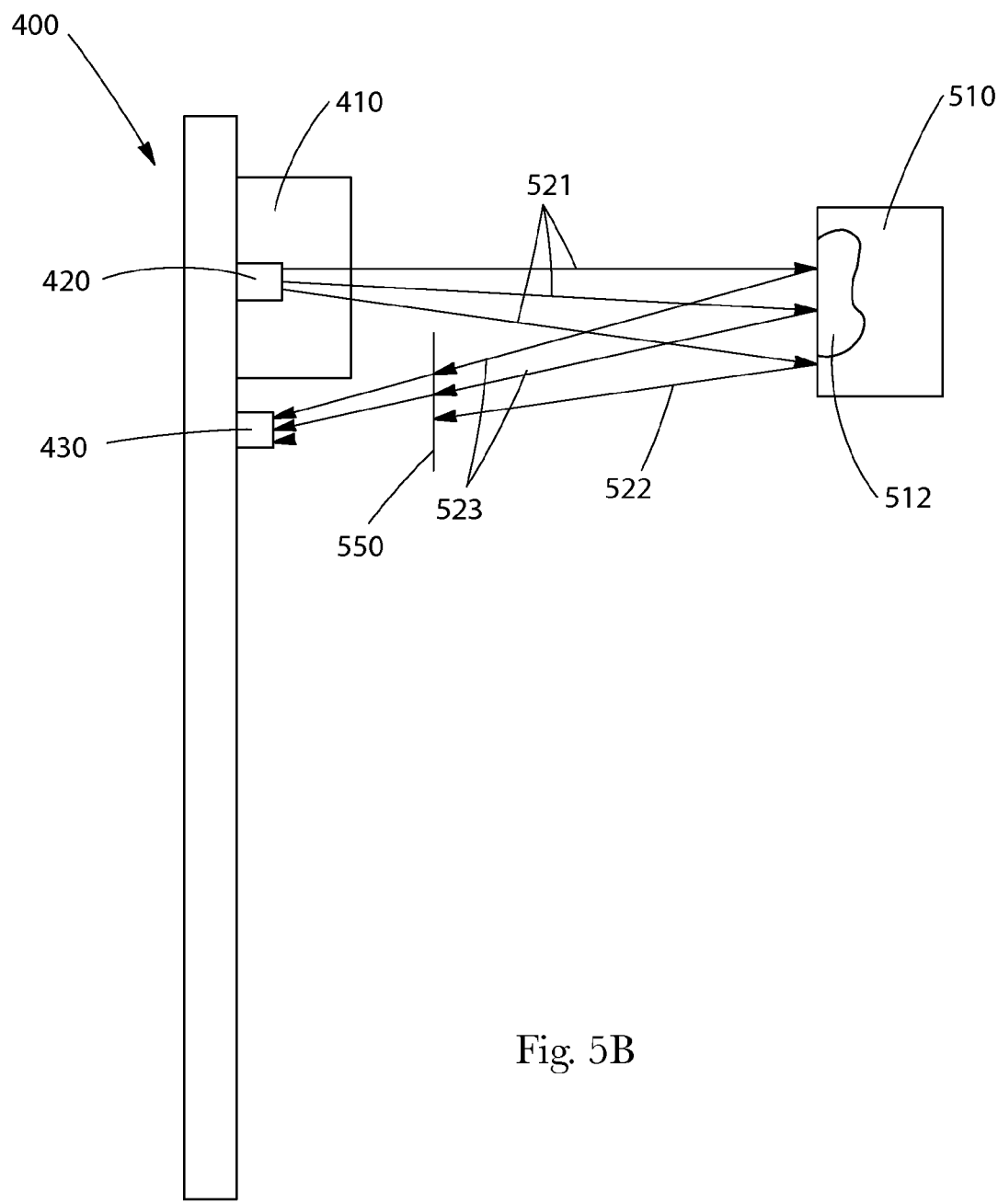
FIG. 5B is a depiction of a toothbrush that is part of a personal hygiene device according to one embodiment of the present invention and a tooth, wherein a filter is disposed between the tooth and the toothbrush.

Accordingly, as shown in FIG. 5B, certain embodiments incorporate at least one filter 550 within the electromagnetic energy path between tooth 510 and detection device 430. Filter 550 may be selected such that the intensity of reflected electromagnetic energy 522 is reduced at detection device 430. Reflected electromagnetic energy 522 downstream of filter 550 may have an intensity which is at least about 5% less than that of the intensity of reflected electromagnetic energy 522 upstream of filter 550, about 10% less, about 15% less, about 20% less, about 25% less, about 30% less, about 35% less, about 40% less, about 45% less, about 50% less, about 55% less, about 60% less, about 65% less, about 70% less, about 75% less, about 80% less, about 90% less, about 95% less, or about 99% less. The incorporation of filter 550 can reduce the margin for error in detection device 430.

Some embodiments incorporate filter 550 between electromagnetic source 420 and tooth 510. Other embodiments, as depicted in FIG. 5B, incorporate filter 550 between tooth 510 and the detection device 430. Yet other embodiments incorporate a first filter between electromagnetic source 420 and tooth 510 and a second filter between tooth 510 and detection device 430. Embodiments of personal hygiene device 100 may include any number and variety of filters between electromagnetic source 420 and detection device 430. Additional embodiments utilize lenses between electromagnetic energy source 420 and tooth 510 and/or between tooth 510 and detection device 430. Any lenses incorporated between electromagnetic energy source 420 and tooth 510 can focus the emitted electromagnetic energy 521 upon a particular oral surface. Similarly, lenses incorporated between tooth 510 and detection device 430 can focus the fluorescent energy 523 upon detection device 430.

In general, dichroic filters usually reflect portions of light which are not wanted and transmit the remainder. Bandpass filters generally filter/block wavelengths of electromagnetic energy outside of a selected interval of wavelengths. The bandpass filter may comprise a laminate structure having multiple filtering layers, e.g. a blue filter and a green filter. Longpass filters may filter/block shorter wavelengths and transmit longer wavelengths over a range of a selected spectrum, e.g. ultraviolet, visible, or infrared.

Any suitable filter known in the art may be utilized in the personal hygiene device. Non-limiting examples include films, sheets, substrates, laminates, mirrors, mirror reflectance filters, lenses, eye glasses, eye goggles, dichroic filters, interference filters, band pass filters, optical long pass filters, filtering viewing surfaces, filtering reflective surfaces, filtered viewing devices, filtered reflective surfaces and/or combinations thereof, and other known or unknown devices operable to filter or block predetermined wavelengths of energy. A suitable example of a mirror which can be utilized in the present invention is available from American Acrylics located in Skokie, Ill., and sold as Yellow Acrylic Mirror #2208. Other suitable examples of filters which can be utilized in the personal hygiene device are available from Roscolux located in Stamford, Conn. and sold as #312 Canary, #12 Straw, #11 Light Straw. Further examples of suitable filters for use in the present invention are available from GamColor located in Los Angeles, Calif. and sold as 480 Medium Yellow 88% T, and 460 Mellow Yellow 83% T. Still further suitable examples of filters for use with the present invention, although less efficient than the aforementioned filters, available from Roscolux are #06 No Color Straw, #07 Pale Yellow, #13 Straw Tint and available from GamColor 440 Very Light Straw.

As mentioned previously, the mechanism for identifying biological deposits may also involve secondary fluorescence. Accordingly, electromagnetic energy source 420 may be selected to elicit fluorescence emissions from a particular chemistry, e.g. a disclosing agent. In secondary fluorescence, an oral composition comprising a disclosing agent may be utilized in the oral cavity. This disclosing agent may attach, diffuse into, bind with, and/or saturate plaque or some other biological deposit such that when exposed to electromagnetic energy, the disclosing agent emits fluorescence. Non-limiting examples of suitable oral compositions having disclosing agents are disclosed in U.S. Pat. Nos. 3,309,274; 3,309,274; 4,266,535; 3,723,613; 4,348,378; 4,459,277; 5,190,743 and 5,862,559; U.S. Patent Application Ser. Nos. 60/858,504 filed on Nov. 13, 2006 and 60/932,880 filed on Jun. 12, 2007; and international patent application serial number IB 2007/054597, which are all hereby incorporated by reference in their entirety.

More specifically, non-limiting examples of suitable disclosing agents include fluoroscein, dibromofluoroscein, tribromofluoroscein, tetrabromofluoroscein, other fluorescein derivatives (including salts thereof), xanthenes, riboflavin, thiamine, niacin, B-vitamins, quinine, pyrenes, e.g. pyranine, D&C Blue No. 1, D&C Blue No. 2, D&C Green No. 3, D&C Red No. 3, D&C Red No. 6, D&C Red No. 7, D&C Red No. 21, D&C Red No. 22, D&C Red No. 27, D&C Red No. 28, D&C Red No. 33, D&C Red No. 40, D&C Yellow No. 5, D&C Yellow No. 6, D&C Yellow No. 10, combinations thereof or any other dye approved for use in drugs and cosmetics by regulatory agencies such as, for example, The United States Food and Drug Administration. Other suitable disclosing agents may include dyes sold under the trade name Alexafluor™ by Invitrogen Corporation located in Carlsbad, Calif. Some examples of disclosing agents which generally exhibit excitation when exposed to blue light are dibromofluorescein, fluorescein, riboflavin, pyranine. These disclosing agents are available from Spectrum Chemical located in Gardena, Calif., United States. However, any suitable disclosing agent may be utilized to identify biological deposits through secondary fluorescence.

The concentration of the disclosing agent in the oral composition can be selected so that the conditions within the oral cavity are not readily visually perceptible under ambient light but becomes more visually perceptible when electromagnetic energy is applied to the oral cavity from electromagnetic energy source 420. Note that the electromagnetic energy supplied by electromagnetic energy source 420 may be in addition to the ambient light or may be in the absence of ambient light. The concentration of the disclosing agent may depend, in part, on the particular disclosing agent selected, with possibly lesser amounts being needed for disclosing agents absorbing or outputting greater fluorescent energy, and conversely, greater amounts may be needed for disclosing agents which output less fluorescent energy. Additionally, the concentration of the disclosing agent may depend, in part, on the oral condition to be identified, the ability of the disclosing agent to be incorporated into the specific carrier, e.g. mouthrinse, dentifrice, etc., and where the condition to be identified is plaque, the ability of the disclosing agent to attach, diffuse into, bind with, and/or saturate the plaque.

In some embodiments, the concentration of the disclosing agent in the oral composition may range from about 0.001% by weight to about 5% by weight, or any individual number within the range. In some embodiments, the concentration of the disclosing agent can be greater than about 0.001% by weight, greater than about 0.003% by weight, greater than about 0.005% by weight, greater than about 0.007% by weight, greater than about 0.009% by weight, greater than about 0.01% by weight, greater than about 0.02% by weight, greater than about 0.03% by weight, greater than about 0.04% by weight, greater than about 0.05% by weight, greater than about 0.06% by weight, greater than about 0.07% by weight, greater than about 0.08% by weight, greater than about 0.09% by weight, greater than about 0.1% by weight, greater than about 0.165% by weight, greater than about 0.2% by weight, greater than about 0.3% by weight, greater than about 0.4% by weight, greater than about 0.5% by weight, greater than about 0.6% by weight, greater than about 0.7% by weight, greater than about 0.8% by weight, greater than about 0.9% by weight, greater than about 1% by weight, greater than about 1.5% by weight, greater than about 2% by weight, greater than about 2.5% by weight, greater than about 3% by weight, greater than about 3.5% by weight, greater than about 4% by weight, greater than about 4.5% by weight and/or less than about 5% by weight, less than about 4.5% by weight, less than about 4% by weight, less than about 3.5% by weight, less than about 3% by weight, less than about 2.5% by weight, less than about 2% by weight, less than about 1.5% by weight, less than about 1% by weight, less than about 0.9% by weight, less than about 0.8% by weight, less than about 0.7% by weight, less than about 0.6% by weight, less than about 0.5% by weight, less than about 0.4% by weight, less than about 0.3% by weight, less than about 0.2% by weight, less than about 0.1% by weight, less than about 0.09% by weight, less than about 0.08% by weight, less than about 0.07% by weight, less than about 0.06% by weight, less than about 0.05% by weight, less than about 0.04% by weight, less than about 0.03% by weight, less than about 0.02% by weight, or less than about 0.01% by weight.

In addition to the disclosing agent, oral care compositions may include a carrier for delivering the disclosing agent to the oral cavity. Some suitable examples of carriers for delivering the disclosing agent to the oral cavity include toothpaste, tooth gel, dentifrices, tooth powders, mouthwashes, rinses, mouth sprays, lozenges, gum, sachets, dental solutions, irrigation fluids, and combinations thereof.

The previous discussion with regard to FIGS. 5A and 5B is equally applicable to the embodiments incorporating secondary fluorescence disclosed above. As such, toothbrush 400, as depicted in FIGS. 5A and 5B and/or filter 550 (shown in FIG. 5B), may be utilized in conjunction with an oral composition incorporating a disclosing agent. Accordingly, a user provides an oral composition comprising a disclosing agent to the oral cavity. The disclosing agent is then exposed to the emitted electromagnetic energy from electromagnetic energy source 420. Without wishing to be bound by theory, it is believed that the disclosing agent absorbs at least a portion of the electromagnetic energy and reflects a portion of the electromagnetic energy. The disclosing agent also emits electromagnetic radiation having a different wavelength or range of wavelengths than that of the electromagnetic energy emitted by electromagnetic energy source 420. The secondary fluorescence may produce a visible color contrast between clean tooth surfaces and the biological deposits and/or produce detectable wavelength contrast between clean tooth surfaces and the biological deposits.

As discussed above, auto-fluorescence or secondary fluorescence techniques may be utilized with personal hygiene device 100. Any suitable instruments may be utilized in auto-fluorescence or secondary fluorescence. Some suitable examples of auto-fluorescence are provided in U.S. Pat. Nos. 5,894,620; 6,485,300; 5,382,163; 6,102,704; 5,590,660; 6,024,562; 6,186,780; and German reference nos. DE29704185; DE29705934, which are all hereby incorporated by reference in their entirety. Some suitable examples of secondary fluorescence are provided in U.S. Pat. Nos. 3,309,274; 5,894,620; WIPO publication no. WO 1992/006671A1; and European Patent Application Publication No. EP56877A1, which are all hereby incorporated by reference in their entirety.

Electromagnetic energy source 420 (shown in FIGS. 4A-4B, 5A-5B, and 6A-6B) may be disposed in any suitable location on toothbrush 400. For example, electromagnetic energy source 420 may be disposed in the head, the handle, or the neck of toothbrush 400. Additionally, embodiments are contemplated where electromagnetic energy source 420 is disposed within the body of toothbrush 400. In such embodiments, the body of toothbrush 400 may be made of translucent material and/or toothbrush 400 may comprise light guides which transmit the energy from electromagnetic energy source 420 to a location outside of the body of toothbrush 400.

Electromagnetic energy source 420 may emit electromagnetic radiation in any suitable direction. For example, as shown in FIGS. 4A and 4B, some embodiments toothbrush 400 include electromagnetic energy source 420 that emits radiation in a direction which is generally parallel to cleaning element field 410. However, some embodiments of toothbrush 400 include electromagnetic energy source 420 that emits radiation from other surfaces of toothbrush 400 (e.g., the backside surface of toothbrush 400).

Additionally, embodiments are contemplated where toothbrush 400 comprises more than one electromagnetic energy source. In such embodiments, a second electromagnetic energy source may have an emission spectrum which is different than that of electromagnetic energy source 420, thereby inducing fluorescence in a biological deposit which is not induced by electromagnetic energy source 420. Additionally, embodiments are contemplated where each of the electromagnetic energy sources may be selected to induce fluorescing within a particular disclosing agent. For example, an oral care composition comprising more than one disclosing agent may be utilized to highlight different biological deposits. By utilizing a toothbrush with more than one electromagnetic energy source, each of the disclosing agents may be excited by their respective electromagnetic energy sources and fluoresce approximately simultaneously. Also, some embodiments include electromagnetic energy source 420 that emits electromagnetic energy in a direction which is generally parallel to cleaning element field 410 and a second electromagnetic energy source that emits electromagnetic energy from the backside surface of toothbrush 400.

Regardless of whether auto-fluorescence or secondary fluorescence is utilized, toothbrush 400 may be utilized with a position member of a personal hygiene device. As shown in the non-limiting example of FIG. 6A, toothbrush 400 may be used in conjunction with position member 690. In some embodiments, position member 690 includes receiving unit 40 and display device 30 and a detection device 430. Each of receiving unit 40 and display device 30 may be constructed as discussed previously. Toothbrush 400 may be in signal communication with receiving unit 40. For ease of explanation, discussion regarding FIGS. 6A and 6B shall be in the context of secondary fluorescence. However, auto fluorescence can similarly be applied to the embodiments of FIGS. 6A and 6B.

Figure 6A:
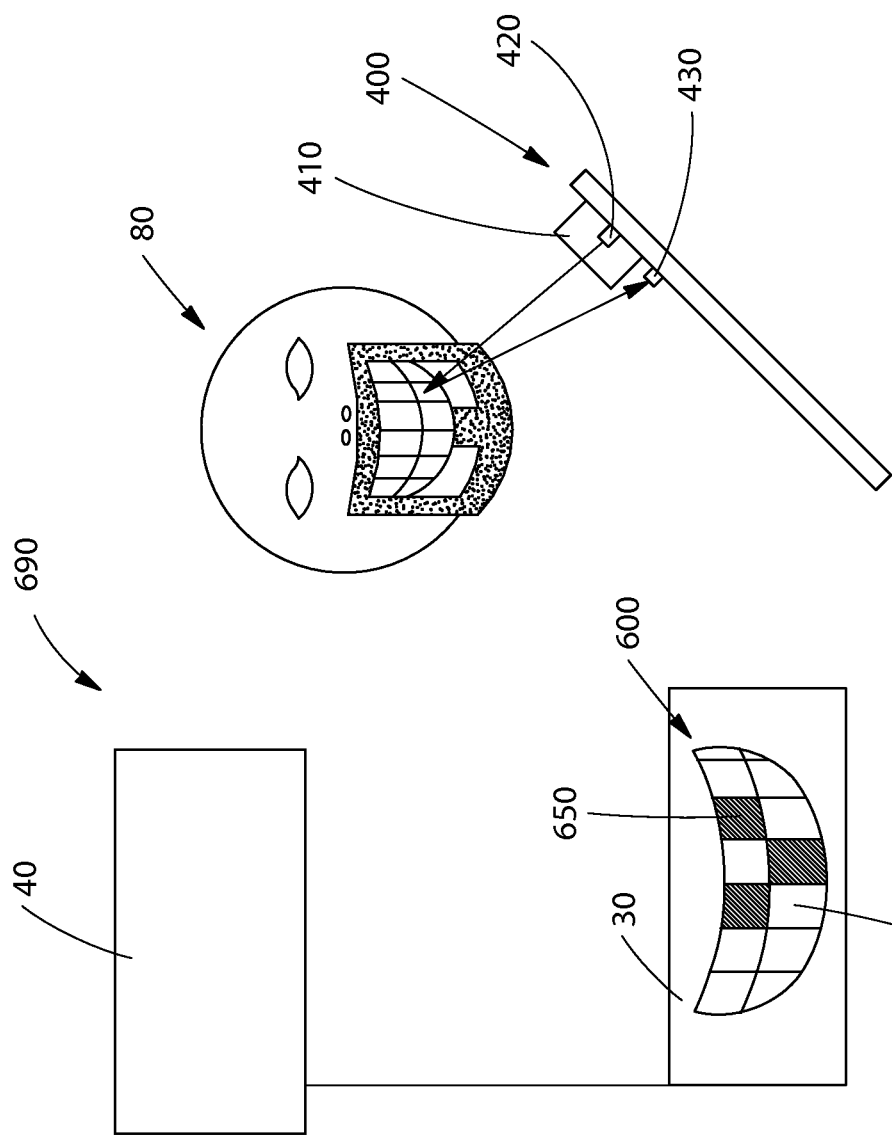
FIG. 6A is a view of a personal hygiene device according to one embodiment of the present invention that includes a receiving unit and a display device that displays a simulated oral cavity.

Still referring to FIG. 6A, electromagnetic energy source 420 can emit electromagnetic radiation which impinges on a tooth surface or other oral surfaces or on a disclosing agent in the oral cavity. The disclosing agent can emit fluorescent energy thereby causing a visual contrast or a detectable contrast between biological deposit and a clean tooth surface. Detection device 430 may provide image data of the oral cavity with the electromagnetic energy applied thereto to receiving unit 40. As discussed previously, oral cavity features may be utilized to measure the location and/or orientation of the head of user 80 and the location and/or orientation of toothbrush 400.

By processing the image data from detection device 430 regarding location and/or orientation of the head of user 80 and the location and/or orientation of toothbrush 400, receiving unit 40 can send image data to display device 30 such that visual representation 600 of simulated oral cavity is shown on display device 30. Additionally, by processing the image data from detection device 430, the contrast between the biological deposits and the clean tooth surfaces can be identified such that display device 30 may provide visual representation 600 which identifies and/or highlights the biological deposits of the oral cavity. As shown in FIG. 6A, teeth of first color 650 may designate teeth which are yet to be effectively brushed and teeth of second color 670 may designate teeth which have been effectively brushed. Any colors may be utilized for first color 650 and second color 670 and such colors should be distinguishable from one another. In some embodiments, a third color or more can be utilized to indicate teeth which have been brushed but have residual biological matter deposited thereon. Additionally, other embodiments provide image data of the oral cavity to the receiving unit 40 as a real time image transmitted from a camera (detection device 430) on toothbrush 400 to receiving unit 40. In this manner, an actual image of the oral cavity may be shown by display device 30 as opposed to a simulated image.

Figure 6B:
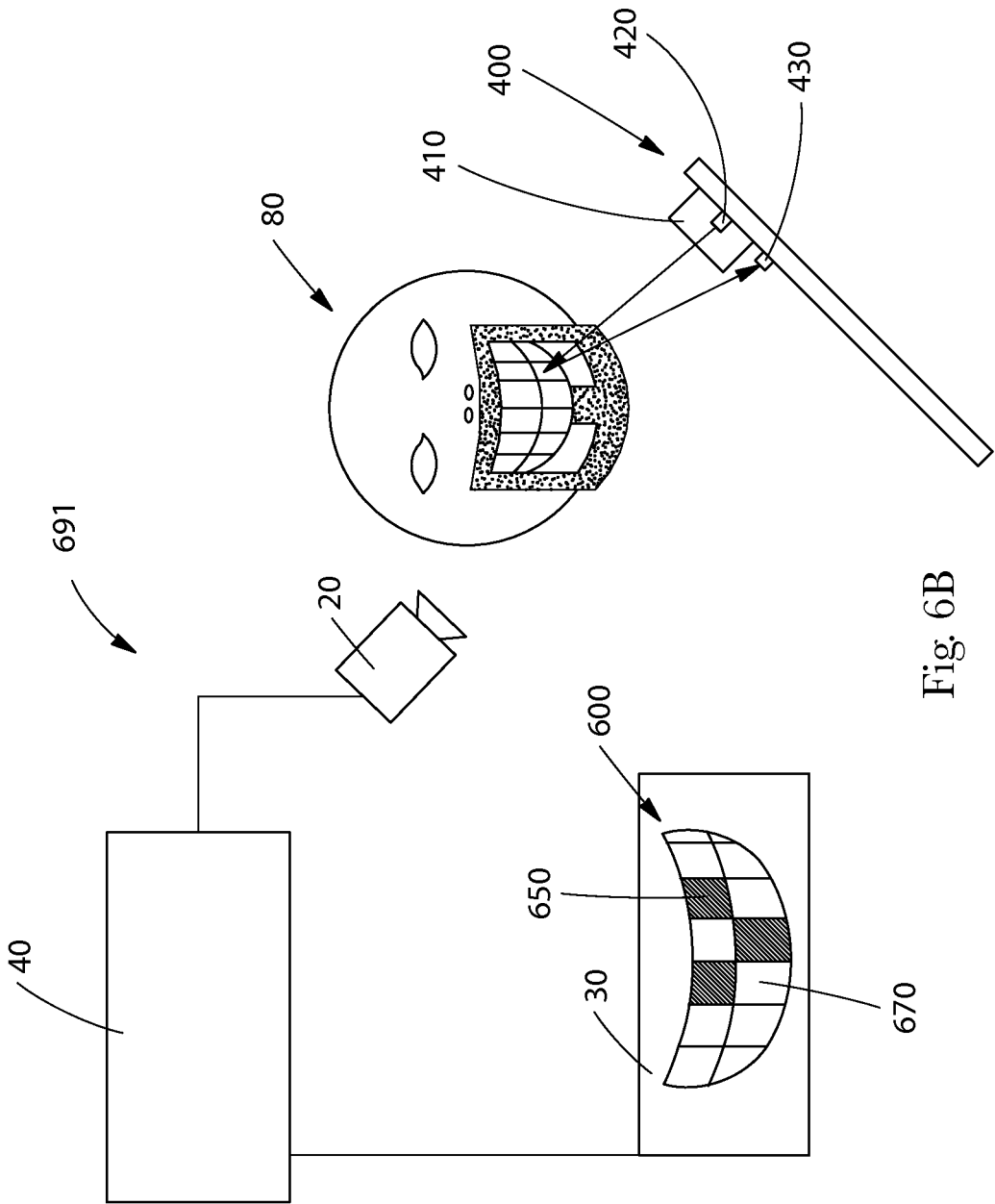
FIG. 6B is a view of a personal hygiene device according to one embodiment of the present invention that includes a receiving unit, a camera, and a display device that displays a simulated oral cavity.

In some embodiments, detection device 430 may not comprise a camera but may be a semiconductor photosensor. In such embodiments, the location and/or orientation of the head of user 80 and the orientation and/or location of toothbrush 400 may not be obtainable without the use of an additional camera as discussed with regard to position member 90 (shown in FIG. 1) and as described with regard to FIGS. 1-3. As shown in FIG. 6B, position member 691, constructed similarly to position member 90, may be utilized to obtain the location and/or orientation of the head of user 80 and the location and/or orientation of toothbrush 400 along with the image data discussed herein with regard to the detection device 430.

The embodiments discussed with regard to FIGS. 4A and 4B, 5A and 5B, and 6A and 6B, can assist the user in their oral hygiene routine. Specifically, by providing a visual representation of the oral cavity, either actual or virtual, user 80 can view any oral surfaces which have not been cleaned or that have remaining biological deposits on them. As such, the personal hygiene device of the present invention can influence the oral hygiene of the user 80 in a positive way. For those embodiments which do not provide visual feedback to the user 80, the feedback which is provided (e.g. vibration, visual, etc.) can similarly influence the oral hygiene of the user 80 in a positive manner.

Another benefit to utilizing the embodiments of oral hygiene device of the present invention may be that the user develops a more efficient and/or a more thorough oral hygiene routine. For example, receiving unit 40 may be configured to track the oral surfaces missed or those oral surfaces which are not cleaned well over a predetermined number of uses. In subsequent oral hygiene routines, receiving unit 40 may provide data to display device 30 highlighting those areas which are traditionally not cleaned well. Due to the highlighted areas, the user may pay closer attention to their oral hygiene routine when they are performing their cleaning operation on the highlighted area.

In some embodiments, an additional benefit is that position members 90, 690, 691, as described herein, are able to transfer data to the user's dental professional. For example, the receiving unit 40 may be capable of utilizing the Internet to transmit image data and/or statistical data regarding brushing, flossing, irrigating, and combinations thereof, to the user's dental professional for evaluation. Accordingly, during office-visits, the dental professional may consider the user's personal oral hygiene routine and evaluate accordingly. Moreover, other embodiments configure position members 90, 690, and 691, as described herein, to communicate with a portable storage device. For example, receiving unit 40 may comprise a USB port which allows a user to download image data and/or statistical data (as described above) to a portable storage device. That image data and/or statistical data can then be presented to the dentist for evaluation of the user's personal hygiene technique or can assist the dentist in assessing the condition of the oral cavity of the user 80. Additionally, embodiments are contemplated where position members 90, 690, and 691, as described herein, can store multiple image and/or statistical data files for multiple individuals.

Other embodiments include the ability to track change in oral surfaces, e.g. tissues, over time. For example, position members 90, 690, and 691, described herein, may be configured to compare hard and soft tissues. Over a predetermined period of time, the position members may be configured to compare gumlines of specific teeth, as well as measure the amount of tooth enamel shown versus the amount of soft tissue shown. Therefore, personal hygiene device 100 may record gum recession and dentin exposure data for evaluation by a user or a dental professional. This function could be useful in early detection of gingivitis.

Electromagnetic energy source 420 may be any suitable electromagnetic energy source. Some non-limiting examples include a light-emitting element. A wide variety of light-emitting elements may be used with the present invention. For example, the light-emitting elements can be a small, low power consumption, light emitting diodes (LEDs) such as those commercially available under the designation Luxeon™ manufactured by Lumileds Lighting, LLC of San Jose Calif. Other commercially available light-emitting elements include those from American Opto Plus LED Corp. and from LiteOn Corp. sold under the tradename LTL42TBKL14-1B2. The LED can operate from a relatively low voltage DC power supply, such as greater than about 0.1 volts to about 9 volts. In some embodiments, the LED may operate from a voltage of greater than about 0.1 volts, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 5.5, 6.0, 6.5, 7, 7.5, 8, 8.5, and/or less than about 9, 8.5, 8, 7.5, 7, 6.5, 6, 5.5, 5, 4.5, 4, 3.5, 3, 2.5, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1 volts. The light-emitting element may have a diameter of greater than about 0.5, 1, 2, 3, 4, 5, 6, 7, 8, 10, 15, 20 mm and/or less than about 20, 15, 10, 8, 7, 6, 5, 4, 3, 2, or 1 mm.

Additionally, suitable electromagnetic energy sources may emit a wide variety of energy intensities. Any suitable intensity may be utilized. There are several parameters which may be utilized to identify the intensity, flux density, etc., of the energy emission from the LED. For example, Flux Density at a Representative Tooth Surface (FDRT), Percent Total Luminous Flux Within a Solid Angle, Half Angle and/or Viewing Angle, Emission Temperature, and Power Dissipation, can be measured in accordance with the procedure described in U.S. Patent Application Publication No. 2005/0053895, which is hereby incorporated by reference in its entirety.

Detection device 430 (shown in FIGS. 4A-4B, 5A-5B, and 6A-6B) may be disposed in any suitable location on toothbrush 400. For example, detection device 430 may be disposed in the head, the neck, or the handle of toothbrush 400. Embodiments are also contemplated where detection device 430 is disposed within the body of toothbrush 400. In such embodiments, the body of toothbrush 400 may be made of translucent material and/or toothbrush 400 may comprise light guides which receive the energy from a location outside of the body of toothbrush 400. Additionally, embodiments are contemplated where toothbrush 400 comprises multiple detection devices each of which may be selected to detect the presence of particular wavelengths of light. The multiple detection devices may be used in conjunction with or independently of the multiple electromagnetic energy sources as discussed above, and/or the multiple disclosing agents as discussed above.

Any suitable detection device may be utilized. For example, as discussed previously, the detection device may comprise a semiconductor photodiode and/or light sensors. An example of a suitable light sensor is commercially available from TAOS, Inc., of Plano, Tex., under the designation No. TSL12S.

Cleaning element field 410 (shown in FIGS. 4A and 4B, 5A and 5B, and 6A and 6B) may comprise any suitable cleaning and/or massaging elements known in the toothbrush art. For example, a first portion of cleaning element field 410 may comprise bristles while a second portion of cleaning element field 410 may comprise an elastomeric cleaning element or an elastomeric massaging element. Any suitable type of bristle may be utilized, any suitable elastomer may be utilized, and in any configuration of the bristles and/or the elastomers. For example, the bristles may comprise an abrasive and/or a slip agent, (for example, Teflon®) or combinations thereof. The bristles may have a round cross section or may have a polygonal cross section. The bristles or a portion thereof may be crimped, may comprise dimples, may be end rounded, may be flagged, or combinations thereof. The elastomers may comprise an abrasive and/or a colorant. Some suitable examples of bristles, elastomers, configurations of bristles and/or elastomers, are provided in U.S. Pat. Nos. 5,313,909; 5,565,206; 5,722,106; 5,906,834; 6,018,840; 5,735,011; and U.S. Patent Application Publication No. 2006/0085931, which are hereby incorporated by reference in their entirety. Additionally, cleaning element field 410 may include pivoting elements as described in U.S. Pat. No. 6,553,604 and U.S. Patent Application Publication No. 2007/0251040, which are hereby incorporated by reference in their entirety.

Additionally, the handle and/or the neck of toothbrush 400 may be constructed in any suitable manner out of any suitable material or combinations of materials. For example, toothbrush 400 may include a first portion comprising polypropylene and a second portion comprising an elastomer. The elastomer used in the handle and/or neck may be the same or different than any elastomer utilized in the head, if any. Moreover, some embodiments of toothbrush 400 include a motor for imparting motion to a bristle carrier as disclosed in U.S. Patent Application Publication No. 2005/0050659, or may include a motor having an eccentric weight as described in U.S. Patent Application Publication No. 2007/0251040, which are both hereby incorporated by reference in their entirety.

Shaving Embodiments

Some embodiments of the personal hygiene device include a razor, shaver or trimmer as a personal hygiene implement (e.g., personal hygiene implement 10, 400). In such embodiments, a receiving unit (e.g., receiving unit 40) can track and monitor the grooming status (e.g., untrimmed, trimmed or shaven) of a user's facial or body hair during a personal hygiene routine based upon gathered position data for the razor/shaver/trimmer and the face and/or body of a user as shown and described above herein with reference to the oral hygiene exemplary embodiments. Additionally, the receiving unit may provide image data to a display device (e.g., display device 30) which provides a visual representation (e.g., virtual representation 300, 600) of the user's face and/or body and the presence or absence of hair, both trimmed and untrimmed.

As previously discussed in detail, through recognition of designated features, a position member (e.g., position member 90, 690, 691) may recognize a user's face and/or body, as well as a personal hygiene implement. As a non-limiting example, a camera (e.g., camera 20) may transmit image data regarding the face and/or body of a user to a receiving unit (e.g., receiving unit 40). Based upon the image data and the designated features selected, the receiving unit may determine the location/orientation of the face and/or body of the user. Similarly, the camera may also transmit image data regarding the razor/shaver/trimmer to the receiving unit. Based upon the image data and the designated features selected, the receiving unit may determine the location/orientation of the razor/shaver/trimmer. The receiving unit may then track the path of the razor/shaver/trimmer to identify the shaving or trimming routine and/or the grooming status of a user's facial and/or body hair.

The receiving unit may process the image data and provide that processed data to the display device. Regardless of the type of image data transferred to the display device, a visual representation provided on the display device can assist the user in their personal hygiene routine. The display device may provide a real time image of a user's face and/or body, an image of the user's face and/or body previously stored in the receiving unit, a generic face and/or body image of a male or female user, or a visual representation of a simulated portion of the user's face and/or body. The visual representation (e.g., visual representation 300, 600) may include different colored areas of the face and/or body to indicate grooming status. For example, in certain embodiments, areas of the face and/or body in a first color (e.g., first color 310, 650) may designate areas which are yet to be shaven, and areas of the face and/or body in a second color (e.g., second color 320, 670) may designate areas which have been shaven. Obviously, any colors may be utilized for the first color and the second color, and such colors should be distinguishable from one another. In some embodiments, a third color may be utilized to indicate portions of user's face and/or body that were shaven or trimmed, but not effectively shaven or trimmed (e.g., hair still remains on a portion of the user's face and/or body that was contacted by the shaver). In alternate embodiments, any number, varieties and shades of colors may be utilized to indicate any number or variety of statuses of particular portions of the face and/or body.

A benefit of the shaving/trimming embodiments disclosed herein may be that the user develops a more efficient and/or a more thorough shaving/trimming routine. For example, the receiving unit may be configured to track the facial or body surfaces missed or those facial or body surfaces which are not shaven or trimmed effectively over a predetermined number of uses. In subsequent shaving/trimming routines, the receiving unit may provide data to the display device highlighting those areas which are traditionally missed or not shaven or trimmed effectively. Due to the highlighted areas, the user may pay closer attention to their shaving/trimming routine when they are performing their shaving/trimming operation on the highlighted areas.

Another benefit of the shaving/trimming embodiments disclosed herein may be that the user develops a shaving/trimming routine that provides a more neat and/or symmetrical appearance to facial or body hair. For example, the receiving unit may be configured to track a user's facial hair to compare the right and left sides of the user's face to ensure that both sides of the user's facial hair are even and symmetrical. If a user's facial hair is asymmetrical, the display device can highlight such irregularities and provide correcting images and/or instructions (e.g., the length of one of the user's sideburns is different from its counterpart). In additional embodiments, a complete set of shaving and/or trimming instructions could be displayed on the display device to assist a user as they shave a particular style of facial or body hair (e.g., goatee, mustache, beard).

Face and Body Washing Embodiments

Some embodiments of the personal hygiene device include a wash implement (e.g., sponge and/or washcloth) as a personal hygiene implement (e.g., personal hygiene implement 10, 400). In such embodiments, a receiving unit (e.g., receiving unit 40) can track and monitor the washing status (e.g., washed or unwashed) of a user's face and/or body during a personal hygiene routine based upon gathered position data for the wash implement and the face and/or body of a user as shown and described above herein with reference to the oral hygiene exemplary embodiments. Additionally, the receiving unit may provide image data to the display device (e.g., display device 30) which provides a visual representation (e.g., virtual representation 300, 600) of the user's face and/or body and the washing status of the user's face and/or body.

As previously discussed in detail, through recognition of specific designated features, the position member (e.g., position member 90, 690, 691) may recognize a user's face and/or body, as well as the personal hygiene implement. As a non-limiting example, a camera (e.g., camera 20) may transmit image data regarding the face and/or body of a user to a receiving unit (e.g., receiving unit 40). Based upon the image data and the designated features selected, the receiving unit may determine the location/orientation of the face and/or body of the user. Similarly, the camera may also transmit image data regarding the wash implement to a receiving unit. Based upon the image data and the designated features selected, the receiving unit may determine the location/orientation of the wash implement. The receiving unit may then track the path of the wash implement to identify the washing routine and/or the washing status of a user's face and/or body. Alternately, through the image data provided by the camera, the receiving unit may also utilize object recognition to determine the washing status of a user's face and/or body.

The receiving unit may process the image data and provide that processed data to the display device. Regardless of the type of image data transferred to the display device, a visual representation (e.g., visual representation 300, 600) provided on the display device can assist the user in their personal hygiene routine. The display device may provide a real time image of a user's face and/or body, an image of the user's face and/or body previously stored in the receiving unit, a generic face and/or body image of a male or female user, or a visual representation of a simulated portion of the user's face and/or body. The visual representation may include different colored areas of the face and/or body to indicate washing status. For example, in certain embodiments, areas of the face and/or body in a first color (e.g., first color 310, 650) may designate areas which are yet to be washed, and areas of the face and/or body in a second color (e.g., second color 320, 670) may designate areas which have been washed. Obviously, any colors may be utilized for the first color and the second color, and such colors should be distinguishable from one another. In some embodiments, a third color may be utilized to indicate portions of user's face and/or body that were washed, but not effectively washed (e.g., dirt or oil still remains on a portion of the user's face and/or body that was contacted by the wash implement). In alternate embodiments, any number, varieties and shades of colors may be utilized to indicate any number or variety of statuses of particular portions of the face and/or body.

A benefit of the washing embodiments disclosed herein may be that the user develops a more efficient and/or a more thorough washing routine. For example, the receiving unit (e.g., receiving unit 40) may be configured to track the facial or body surfaces missed or those facial or body surfaces which are not washed effectively over a predetermined number of uses. In subsequent washing routines, the receiving unit may provide data to the display device highlighting those areas which are traditionally missed or not washed effectively. Due to the highlighted areas, the user may pay closer attention to their washing routine when they are performing their washing operation on the highlighted areas.

Cosmetic Application/Removal Embodiments

Some embodiments of the personal hygiene device include a cosmetics brush or applicator as a personal hygiene implement (e.g., personal hygiene implement 10, 400). In such embodiments, a receiving unit (e.g., receiving unit 40) can track and monitor the application and/or removal status of cosmetics to a user's face and/or body during a personal hygiene routine based upon gathered position data for the cosmetics brush/applicator and the face and/or body of a user as shown and described above herein with reference to the oral hygiene exemplary embodiments. Additionally, the receiving unit may provide image data to a display device (e.g., display device 30) which provides a visual representation (e.g., visual representation 300, 600) of the user's face and/or body and the cosmetics application or removal status to the user's face and/or body.

As previously discussed in detail, through recognition of specific designated features, a position member (e.g., position member 90, 690, 691) may recognize a user's face and/or body, as well as the personal hygiene implement. As a non-limiting example, a camera (e.g., camera 20) may transmit image data regarding the face and/or body of a user to a receiving unit (e.g., receiving unit 40). Based upon the image data and the designated features selected, the receiving unit may determine the location/orientation of the face and/or body of the user. Similarly, the camera may also transmit image data regarding the brush/applicator to a receiving unit. Based upon the image data and the designated features selected, the receiving unit may determine the location/orientation of the brush/applicator. The receiving unit may then track the path of the brush/applicator to identify the cosmetics application or removal routine and/or the application or removal status on a user's face and/or body. Alternately, through the image data provided by the camera, the receiving unit may also utilize object recognition to determine the cosmetics application or removal status of a user's face and/or body.

The receiving unit may process the image data and provide that processed data to the display device. Regardless of the type of image data transferred to the display device, a visual representation (e.g., visual representation 300, 600) provided on the display device can assist the user in their personal hygiene routine. The display device may provide a real time image of a user's face and/or body, an image of the user's face and/or body previously stored in the receiving unit, a generic face and/or body image of a male or female user, or a visual representation of a simulated portion of the user's face and/or body. The visual representation may include different colored areas of the face and/or body to indicate cosmetics application or removal status. For example, in certain embodiments, areas of the face and/or body in a first color (e.g., first color 310, 650) may designate areas in which cosmetics are yet to be applied, and areas of the face and/or body in a second color (e.g., second color 320, 670) may designate areas in which cosmetics have been applied. Obviously, any colors may be utilized for the first color and the second color, and such colors should be distinguishable from one another. In some embodiments, a third color may be utilized to indicate portions of user's face and/or body in which cosmetics were applied or removed, but not effectively applied or removed (e.g., in application, cosmetics are still not applied on a particular portion of the user's face and/or body that was contacted by the applicator). In alternate embodiments, any number, varieties and shades of colors may be utilized to indicate any number or variety of statuses of particular portions of the face and/or body. In addition, the personal hygiene device may track multiple varieties of cosmetics on a user's face and/or body at one time.

A benefit of the cosmetics application and removal embodiments disclosed herein may be that the user develops a more efficient application and/or removal routine. For example, the receiving unit (e.g., receiving unit 40) may be configured to track the facial or body surfaces missed or those facial or body surfaces in which cosmetics are not applied effectively or evenly over a predetermined number of uses. In subsequent cosmetics application or removal routines, the receiving unit may provide data to the display device (e.g., display device 30) highlighting those areas in which cosmetics are traditionally not applied effectively or evenly. Due to the highlighted areas, the user may pay closer attention to their cosmetics application routine when they are performing their application or removal operation on the highlighted areas.

Another benefit of the cosmetics application or removal embodiments disclosed herein may be that the user develops a routine that provides a more neat and/or symmetrical application or removal of cosmetics. For example, the receiving unit may be configured to track a user's cosmetic application to compare the right and left sides of the user's face to ensure that both sides of the user's cosmetics application are even and symmetrical. If a user's cosmetic application is asymmetrical, the display device can highlight such irregularities and provide correcting images and/or instructions (e.g., the application of eye shadow to one of the user's eyelid is different from its counterpart).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "500 nm" is intended to mean "about 500 nm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal hygiene device comprising at least one personal hygiene implement and at least one position member that utilizes real time object recognition to identify marker based and markerless designated features on both a user and the personal hygiene implement; and to provide real time feedback to the user, wherein markerless designated features on a user include anatomical landmarks on the body of a user.

2. The personal hygiene device of claim 1, wherein the one or more markerless designated features comprise at least facial landmarks of a user.

3. The personal hygiene device of claim 1, wherein the one or more markerless designated features comprise at least oral cavity landmarks of a user.

4. The personal hygiene device of claim 1, wherein the markerless designated features on the personal hygiene implement include color contrasts, texture contrasts, material contrasts, printed symbols, printed shapes and three dimensional geometry.

5. The personal hygiene device of claim 1, wherein the at least one position member further comprises at least one camera.

6. The personal hygiene device of claim 5, wherein the at least one position member further comprises at least one display device in signal communication with the at least one camera.

7. The personal hygiene device of claim 6, wherein the at least one display device is configured to produce an image of at least a portion of the at least one personal hygiene implement during use.

8. The personal hygiene device of claim 6, wherein the at least one display device is configured to produce at least one of a real time image of at least a portion of a face of a user, an image of at least a portion of a generic face, and an image of at least a portion of a simulated face.

9. The personal hygiene device of claim 6, wherein the at least one display device is configured to produce an image selected from the group consisting of an image of at least a portion of a torso of the user, an image of at least a portion a limb of a user, an image of at least a portion of the users fingers and/or toes, an image of at least a portion of the user's head, and combinations thereof.

10. The personal hygiene device of claim 1, wherein the at least one position member is capable of providing at least one of position and orientation of the personal hygiene implement.

11. The personal hygiene device of claim 1, wherein the marker based designated features include a light emitting diode.

12. The personal hygiene device of claim 11, wherein the light emitting diode emits wavelengths in the infrared portion of the electromagnetic spectrum.

13. The personal hygiene device of claim 1, wherein the at least one personal hygiene implement is a toothbrush.

14. The personal hygiene device of claim 1, wherein the at least one personal hygiene implement is a razor.

15. The personal hygiene device of claim 1, wherein the marker based designated features include mirrors and sound emitters.

* * * * *